(12) United States Patent
Emerson et al.

(10) Patent No.: US 9,248,447 B2
(45) Date of Patent: *Feb. 2, 2016

(54) POLYMERS FOR USE IN CENTRIFUGAL SEPARATION OF LIQUIDS

(75) Inventors: Jane Emerson, Irvine, CA (US); Srinivasa Raghavan, Silverspring, MD (US); Kunshan Sun, Breenbelt, MD (US)

(73) Assignees: The Regents of the University of California, Oakland, CA (US); University of Maryland, College Park, MD (US)

( * ) Notice: Subject to any disclaimer, the term of this patent is extended or adjusted under 35 U.S.C. 154(b) by 1119 days.

This patent is subject to a terminal disclaimer.

(21) Appl. No.: 12/331,277

(22) Filed: Dec. 9, 2008

(65) Prior Publication Data

US 2009/0139937 A1 Jun. 4, 2009

Related U.S. Application Data

(63) Continuation-in-part of application No. 11/499,436, filed on Aug. 4, 2006, now Pat. No. 7,674,388.

(60) Provisional application No. 61/028,426, filed on Feb. 13, 2008, provisional application No. 60/707,299, filed on Aug. 10, 2005.

(51) Int. Cl.
*B01D 21/26* (2006.01)
*B01D 12/00* (2006.01)
*B01L 3/00* (2006.01)
*G01N 33/49* (2006.01)

(52) U.S. Cl.
CPC .......... *B01L 3/50215* (2013.01); *G01N 33/491* (2013.01); *B01D 21/26* (2013.01); *B01L 2200/10* (2013.01); *B01L 2300/0832* (2013.01); *B01L 2300/12* (2013.01); *B01L 2300/1861* (2013.01); *B01L 2400/0409* (2013.01); *B01L 2400/0677* (2013.01); *B01L 2400/086* (2013.01)

(58) Field of Classification Search
None
See application file for complete search history.

(56) References Cited

U.S. PATENT DOCUMENTS

| | | |
|---|---|---|
| 3,647,070 A | 3/1972 | Adler |
| 3,780,935 A | 12/1973 | Lukacs et al. |
| 3,920,549 A | 11/1975 | Gigliello |
| 3,920,557 A | 11/1975 | Ayres |
| 3,976,579 A | 8/1976 | Bennett |
| 4,050,451 A | 9/1977 | Columbus |
| 4,052,320 A | 10/1977 | Jakubowicz |
| 4,101,422 A | 7/1978 | Lamont et al. |
| 4,190,535 A | 2/1980 | Luderer et al. |
| 4,235,725 A | 11/1980 | Semersky |
| 4,295,974 A | 10/1981 | Cornell |
| 4,350,593 A | 9/1982 | Kessler |
| 4,386,003 A | 5/1983 | Fiehler |
| 4,417,981 A | 11/1983 | Nugent |
| 4,569,764 A | 2/1986 | Satchell |
| 4,751,001 A | 6/1988 | Saunders |
| 4,770,779 A | 9/1988 | Ichikawa et al. |
| 4,816,168 A | 3/1989 | Carrol et al. |
| 4,844,818 A | 7/1989 | Smith |
| 4,867,887 A | 9/1989 | Smith |
| 4,946,601 A | 8/1990 | Fiehler |
| 4,994,393 A | 2/1991 | Pradhan et al. |
| 5,124,434 A | 6/1992 | O'Brien |
| 5,266,199 A | 11/1993 | Tsukagoshi et al. |
| 5,304,605 A | 4/1994 | Murakami et al. |
| 5,354,838 A | 10/1994 | Murakami et al. |
| 5,454,958 A | 10/1995 | Fiehler |
| 5,489,386 A | 2/1996 | Saunders |
| 5,494,590 A | 2/1996 | Smith |
| 5,505,853 A | 4/1996 | Satake |
| 5,506,333 A | 4/1996 | O'Brien et al. |
| 5,510,237 A | 4/1996 | Isogawa et al. |
| 5,525,227 A | 6/1996 | Vogler |
| 5,527,843 A | 6/1996 | Murakmi et al. |
| 5,663,285 A | 9/1997 | Rounds |
| 5,731,391 A | 3/1998 | O'Brien et al. |
| 5,776,357 A | 7/1998 | Okamoto et al. |
| 5,814,220 A | 9/1998 | Mikami et al. |
| 5,888,824 A | 3/1999 | Isogawa et al. |
| 5,906,744 A | 5/1999 | Carroll et al. |
| 5,986,039 A | 11/1999 | O'Brien et al. |
| 6,072,022 A | 6/2000 | O'Brien et al. |
| 6,238,578 B1 | 5/2001 | Fiehler |
| 6,280,622 B1 | 8/2001 | Goodrich et al. |
| 6,361,700 B2 | 3/2002 | Gates et al. |
| 6,979,307 B2 | 12/2005 | Beretta et al. |
| 7,090,970 B2 | 8/2006 | Anraku et al. |
| 2006/0160025 A1 | 7/2006 | Lungu |
| 2006/0212020 A1 | 9/2006 | Rainen et al. |
| 2007/0003588 A1 | 1/2007 | Chinn et al. |
| 2007/0005024 A1 | 1/2007 | Weber et al. |
| 2007/0020629 A1 | 1/2007 | Ross et al. |
| 2007/0187341 A1 | 8/2007 | Emerson |
| 2009/0146099 A1 | 6/2009 | Anraku et al. |

FOREIGN PATENT DOCUMENTS

| | | |
|---|---|---|
| EP | 0766973 | 4/1997 |
| JP | H08178236 A | 7/1996 |
| WO | WO2007139018 | 12/2007 |

*Primary Examiner* — Dirk Bass
(74) *Attorney, Agent, or Firm* — Fish & Tsang, LLP

(57) ABSTRACT

Contemplated compositions and methods allow for in-situ formation of a rigid seal layer in a blood collection tube between a cell-depleted phase and a cell-enriched phase. Preferably, the seal layer is formed upon brief UV irradiation and comprises an acrylate, a methacrylate, an epoxy, a urethane, and/or a thiol-ene polymer.

19 Claims, No Drawings

_US 9,248,447 B2_

POLYMERS FOR USE IN CENTRIFUGAL SEPARATION OF LIQUIDS

This application is a continuation-in-part of our copending U.S. application with the Ser. No. 11/499,436, filed Aug. 4, 2006, which claims priority to U.S. provisional application with the Ser. No. 60/707299, and which was filed Aug. 10, 2005. This application further claims the benefit of copending U.S. provisional application with the Ser. No. 61/028426, which was filed Feb. 13, 2008.

FIELD OF THE INVENTION

The field of the invention is photopolymers, and especially photopolymers for separation of cell-containing from cell-depleted biological fluids.

BACKGROUND

Analysis of blood samples often requires separation of whole blood into a serum fraction and a cell-containing fraction. It is well known in the art that whole blood separation can be carried out through centrifugation by disposing whole blood into a blood collection tube, placing the tube into a centrifuge, and spinning down the blood.

Unfortunately, once the blood separates, the fractions of the whole blood can remix causing contamination of the fractions through diffusion, agitation, sample extraction, or other undesirable interaction. Ideally, the two fractions should remain isolated to ensure no contamination occurs when accessing the desired fraction. Furthermore, the analytes of the blood should maintain stability after separation over extended periods of time to provide for storage, shipping, or late term analysis.

Any system that isolates the fractions of whole blood must include a separator substance having a suitable density within the tube. Suitable densities are about 1.04 g/cm$^3$ and are between the density of the heavier cell-containing phase and the density of the lighter serum-containing phase. When whole blood is added to the tube and the tube is centrifuged, the separator substance migrates to between the fractions isolating the two fractions from each other. An example collection tube using a gel as a separator substance and that is flowable with whole blood can be found in U.S. Pat. No. 4,946,601 to Fiehler. These and all other extrinsic references are incorporated herein by reference in their entirety. Where a definition or use of a term in an incorporated reference is inconsistent or contrary to the definition of that term provided herein, the definition of that term provided herein applies and the definition of that term in the reference does not apply. An example separator substance that is also flowable with whole blood can be found in U.S. Pat. Nos. 6,248,844 and 6,361,700 to Gates et. al. In those patents the substance is a polyester curable to a desired viscosity.

Although providing a flowable substance allows for separating the fractions of whole blood, flowable substances have several disadvantages. A flowable substance remains flowable even after centrifugation which results in a risk of contamination of the sample if proper care is not taken to keep the sample suitably still and protected from agitation. For example, it is known to use a thixotropic gel in a blood collection tube where the gel can still flow after centrifugation. Additionally, known substances lack the ability to maintain analytes (e.g., potassium and glucose) at acceptable levels over extended periods of time (e.g., for at least three days).

U.S. Pat. No. 4,818,418 to Saunders discusses the use of a thixotropic gel in blood collection tubes. The problem with thixotropic gels, however, is they do not form a sufficiently permanent separation barrier between the fractions of whole blood. When a sample is extracted from the tube with a pipette, the substance can contaminate or plug the pipette if it touches the substance due to the flowable nature of the substance. If the substance is formulated or configured with a high viscosity to provide a sufficiently solid or permanent barrier to overcome the previous disadvantages, then the substance is no longer suitably flowable with whole blood resulting in prohibitive centrifuge times. Short centrifuge times are critical in life or death situations where a blood analysis result is required quickly.

An alternative approach taken by collection tube manufactures is to provide moveable solid barriers. Examples of suitable solid substances include the intermediate density polymers found in U.S. Pat. Nos. 3,647,070 where polymer spheres form the barrier layer. U.S. Pat. No. 5,266,199 describes a tube-and-ball valve that controls separation of the serum from the cell-containing phase. However, such physical barriers do not provide a sufficient seal between the fractions and are often either incomplete and tend to leak, or impracticable for other various reasons.

These and other solutions for whole blood separation lack the necessary features to ensure the separated factions of whole blood are effectively protected against contamination due to undesirable sample interactions while supporting short centrifugation times. Furthermore, all or almost all of the known separation technologies fail to maintain a stable and permanent barrier that separates the cell-containing phase from the cell-depleted phase. Thus, there is still a need for liquid separation technologies in which the separation layer is a permanent and stable layer that can be formed in a simple and effective manner.

SUMMARY OF THE INVENTION

The inventive subject matter is drawn to various compositions and methods to allow for a rapid formation of a rigid barrier layer in a blood collection tube between a cell-depleted phase and a cell-enriched phase, wherein the barrier layer is preferably formed from a polymerizable composition upon ultraviolet (UV) irradiation.

In preferred aspects of the inventive subject matter, the polymerizable composition has a density and/or flowability effective to allow sterilization prior to use and to allow sedimentation of the composition under a centrifugal force to a position between the cell-depleted phase and the cell-enriched phase. Especially suitable polymers have a density between 1.02 and 1.06 g/cm$^3$ and can be cured to form an acrylate polymer, a methacrylate polymer, an epoxy polymer, a polyurethane, and/or a thiol-ene polymer. It is further generally preferred that the composition includes a photoinitiator and optionally a photoinhibitor. Where needed, the density of the composition can be further adjusted using various ingredients, and suitable ingredients include silica, alumina, and other organic and inorganic filler materials.

In still further preferred aspects, the polymerizable composition allows curing without (a) substantial cell entrapment, (b) substantial shrinkage, (c) excessive heat generation, (d) reacting with one or more blood components to be analyzed, and/or (e) interference with analytic tests performed on the cell-depleted phase and/or cell-enriched phase. It is also generally preferred that the cured polymer has a hardness of at least 10 of a Shore 00, more typically on a Shore A, and most typically Shore D scale, and that the polymer is cured to hardness in less than 60 seconds, and more typically less than 20 seconds. While not limiting to the inventive subject matter, preferred cured polymers will form a fluid-proof barrier between the cured polymer and the inner wall of the collection tube.

Therefore, and viewed from a different perspective, a method of assisting separation of whole blood in a blood collection tube into a cell-depleted phase and a cell-enriched phase is contemplated in which a polymerizable composition is added to the tube, where the composition has a predetermined density and flowability effective to allow sedimentation of the composition under a centrifugal force to a position between the cell-depleted phase and the cell-enriched phase. The tube is then sterilized (e.g., using gamma radiation and/or heat) and evacuated where desired. In a further step of contemplated methods, instructions are then provided to use UV irradiation after centrifugation for a period of less than 30 seconds to cure the polymerizable composition to a hardness of at least 10 on the Shore A hardness scale. With respect to suitable compositions in contemplated methods, the same considerations as provide above apply.

Various objects, features, aspects and advantages of the inventive subject matter will become more apparent from the following detailed description of preferred embodiments.

DETAILED DESCRIPTION

The inventors have discovered various compositions and methods that allow formation of a rigid barrier layer in a blood collection tube from a polymerizable composition upon initiation or acceleration of a polymerization reaction. In preferred aspects, the polymerizable composition has a density and flowability in mammalian blood to allow sedimentation under centrifugal force to a position between a cell-depleted phase and a cell-enriched phase.

One such exemplary composition was previously described in our copending U.S. patent applications with the Ser. Nos. 11/933,839 (published as US 2008/0132874A1), 11/933871 (published as US 2008/0108493A1), and 12/271,610 (filed Nov. 14, 2008), all of which are incorporated by reference herein. Here the composition was a combination of a multifunctional acrylate monomer (trimethylolpropane propoxylate triacrylate), an aliphatic urethane acrylate, and 2,2-Dimethoxy-1,2-diphenyl-ethan-1-one (used as photoinitiator). Fumed silica was added to the composition as a thixotropic agent and to achieve a density of about 1.04 g/cm$^3$. As used herein, the term "about" in conjunction with a numeral refers to a range of that numeral defined by an absolute deviation of 10%, inclusive. For example, the term "about 10 g" refers to a range of 9 to 11, inclusive. Generally, it is preferred that the polymerizable composition will have a density of between about 1.01-1.09 g/cm$^3$, and most preferably 1.03-1.05 g/cm$^3$. Unless a contrary intent is apparent from the context, all ranges recited herein are inclusive of their endpoints, and open-ended ranges should be interpreted to include only commercially practical values. Such polymeric composition exhibited numerous desirable properties, including hardening in less than 10 seconds to a hardness of greater than 10 on a Shore A scale upon UV irradiation while not producing excessive exothermal heat (e.g., did not raise the temperature of the fluid in the tube by more than 5° C.). Moreover, such composition was thixotropic and flowable, and formed a fluid-tight seal with the inside wall of the tube that so isolated the cell-containing phase from the cell-depleted phase. Therefore, preferred compositions will generally have flow properties and a density that allow proper positioning of the polymerizable composition between the cell-depleted phase and the cell-enriched phase, that exhibit low cell trapping and shrinkage, and low or even no exothermic heat generation. Furthermore, preferred composition will allow sterilization (e.g., via gamma rays or steam) without curing the composition to a significant degree (e.g., more than 30% or more than 40% cured).

Of course, it should be appreciated that numerous alternative polymerizable compositions are also deemed suitable for use herein. Most preferably, polymerizable compositions will include those that allow rapid photopolymerization to a hardness of at least 10 on the Shore A scale, typically requiring a curing time of less than 5 minutes. Such polymerizable compositions may homogenous (i.e., comprise a single class of compounds [e.g., acrylate, methacrylate, etc.]), or may be heterogenous (i.e., comprise multiple classes of compounds [e.g., acrylate and epoxy). For example, especially preferred polymerizable compositions will comprise those that are polymerizable (most preferably via by UV irradiation/curing) to an acrylate polymer, a methacrylate polymer, an epoxy polymer, a polyurethane, a thiol-ene polymer, and all reasonable combinations thereof.

For example, where the polymerizable composition is used to form an acrylate polymer and/or methacrylate polymer, suitable compositions will preferably include aliphatic and/or aromatic acrylates and methacrylates, which may have one, and more typically at least two functional acrylate groups (most preferably, all compounds are water soluble to at least some degree). It should be noted that in the following listing of suitable compounds, the term acrylate may also be replaced by the term methacrylate to denote the additional methyl group in the respective acrylate. Among other suitable choices, appropriate acrylates will include monofunctional acrylates, difunctional acrylates, trifunctional acrylates, tetrafunctional and higher acrylates, etc.

Suitable monofunctional acrylates include oxyethylated phenol acrylate, monofunctional epoxy acrylate, phenoxyethyl acrylate, urethane monoacrylate, isobornyl acrylate (tricyclic acrylate), trimethylolpropane acrylate, octyl/decyl acrylate, hydroxypropyl methacrylate, phenoxyethyl acrylate (or other aryloxyalkyl acrylates), substituted cycloalkyl (meth)acrylate (e.g., 3,3,5 trimethylcyclohexyl methacrylate), alkoxylated phenol acrylates, and alkyl methacrylate.

Difunctional acrylates contemplated herein include alpha-omega-alkanedioldiacrylates, alkoxylated aliphatic diacrylates, alkoxylated hexanediol diacrylate, di/tri/polyalkylene glycol diacrylates, di/tri/polyalkylene glycol diacrylates, alkoxylated bisphenol A diacrylates tricyclodecanediol diacrylate, propoxylated neopentyl glycol diacrylate, bisphenol A derivatized diacrylate, dipropylene glycol diacrylate, 1,6-hexanediol diacrylate, and tripropylene glycol diacrylate, while suitable trifunctional acrylates include trimethylolpropane ethoxy triacrylate, acrylated glycerol, trimethylolpropane triacrylate, alkoxylated (and especially ethoxylated or propoxylated) trimethylolpropane triacrylate, and trimethylolpropane triacrylate.

Tetrafunctional and higher acrylates will generally include polyether tetraacrylates, polyester acrylates, dipentaerythritol penta/hexaacrylate, pentaacrylate esters, and ethoxylated pentaerythritol tetraacrylates. Especially suitable oligomeric and polymeric acrylates, including epoxy acrylates, acrylic acrylates, aliphatic urethane acrylates, polyether acrylates, polyester acrylates, acrylate esters, and aliphatic urethane acrylates.

In another example, where the polymerizable composition is used to form an epoxy polymer, suitable compositions will typically include a combination of epichlorohydrin and a polyhydric compound (e.g., bisphenol), and/or one or more compounds that include one, and more typically at least two epoxy groups. Therefore, suitable compounds include monomeric, dimeric, oligomeric, or polymeric epoxy materials containing one or more epoxy groups. In addition to these compounds, one or more reactive diluents may be included to further modify the properties of the desired polymeric material. For example, those resins which result from the reaction of bisphenol-A (4,4'-isopropylidenediphenol) and epichlorohydrin, or by the reaction of low molecular weight phenol-formaldehyde resins with epichlorohydrin, can be used alone or in combination with an epoxy containing compound as a reactive diluent. Suitable diluents include phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc.

Moreover, it should be recognized that contemplated compositions may further include polymeric materials that comprise terminal and/or pendant epoxy groups. Examples of these material are vinyl copolymers containing glycidyl acrylate or methacrylate as one of the co-monomers. Other classes of epoxy containing polymers suitable to cure (preferably using UV curing) are epoxy-siloxane resins, epoxy-polyurethanes and epoxy-polyesters, which typically have epoxy functional groups at the termini. Epoxy-siloxane resins and method for making are more particularly shown by E. P. Pleuddemann and G. Franger, J. Am. Chem. Soc. 81 632-5 (1959). As described in the literature, epoxy resins can also be modified in a number of standard ways such as reactions with amines, carboxylic acids, thiols, phenols, alcohols, etc. as shown in U.S. Pat. Nos. 2,935,488; 3,235,620; 3,369,055; 3,379,653; 3,398,211; 3,403,199; 3,563,850; 3,567,797; 3,677,995; etc. Further examples of epoxy resins which can be used are shown in the Encyclopedia of Polymer Science and Technology, Vol. 6, 1967, Interscience Publishers, New York, pp 209-271.

In a further example, where the polymerizable composition is used to form a urethane polymer (polyurethane), suitable compositions will typically include those that allow formation of urethane links, for example, by reaction of a compound containing at least two isocyanate groups with another compound containing at least two alcohol groups in the presence of a catalyst (e.g., by reaction of polyisocyanates and hydroxyl-containing polyesters).

With respect to suitable isocyanates, it is generally preferred that the isocyanate includes at least two isocyanate groups as such compounds may be used to form polymeric isocyanates having three or more isocyanate functional groups. Most preferably, isocyanates are aromatic isocyanates (e.g., diphenylmethane diisocyanate, toluene diisocyanate, etc.), however aliphatic isocyanates (e.g., hexamethylene diisocyanate, isophorone diisocyanate, etc.) are also expressly contemplated herein. It should be noted that aliphatic and cycloaliphatic isocyanates are less preferred due to the reduced reactivity of the aliphatic isocyanate group as compared to aromatically linked isocyanate groups. Still further contemplated isocyanates include polymeric isocyanates (e.g., diphenylmethane diisocyanate). It should be noted that isocyanates can also be prepared by partial reaction with a polyol to form a prepolymer (i.e., stoichiometric ratio of isocyanate groups to hydroxyl groups is equal to 2:1) or quasi-prepolymer (i.e., stoichiometric ratio of isocyanate groups to hydroxyl groups is greater than 2:1).

With respect to suitable polyols it is contemplated that the polyol is at least a diol, more typically a triol, and most typically a polyol. Short chain or low-molecular weight polyhydric compounds include ethylene glycol, 1,4-butanediol, diethylene glycol, glycerol, and trimethylol propane. Longer chain or higher molecular weight polyhydric compounds include polyether polyols and polyester polyols. For example, flexible polyols have molecular weights from 2,000 to 10,000, while rigid polyols have molecular weights from 250 to 700. Polyols with molecular weights from 700 to 2,000 are often suitable to add stiffness or flexibility to a polymeric system. Among other suitable polyols, especially preferred polyols include polyether polyols and polyester polyols.

Suitable polyether polyols will preferably include dipropylene glycol or glycerol for less rigid barrier layers and sucrose, sorbitol, toluenediamine, and Mannich bases for more rigid barrier layers. Propylene oxide may then be added to achieve a desired molecular weight. Polyols extended with propylene oxide are terminated with secondary hydroxyl groups. In order to change the compatibility, rheological properties, and reactivity of a polyol, ethylene oxide is used as a co-reactant to create random or mixed block heteropolymers. Suitable polyester polyols may be produced by direct polyesterification of diacids and glycols (e.g., adipic acid and 1,4-butanediol), or by use of recycled raw materials, typically via transesterification of recycled poly(ethyleneterephthalate) or dimethylterephthalate with various glycols (e.g., diethylene glycol). Still further contemplated polyols include polycarbonate polyols, polycaprolactone polyols, polybutadiene polyols, and polysulfide polyols.

Additional components to modify the polyurethane include chain di- and higher polyols that can be used as extenders and typically include alkylene glycols (e.g., diethylene, triethylene, etc.), alpha-omega-alkanediols (e.g., 1,3-propanediol, 1,4-butanediol, etc.), diethanolamine, phenyldiethanolamine, etc. Still further contemplated compounds for polyurethanes are found in U.S. Pat. No. 6,747,088.

It is further contemplated that all suitable catalysts for polyurethane formation may be used, and all known catalysts are deemed suitable for use herein. Among other classes, preferred catalysts include amine compounds and organometallic complexes. For example, amine catalysts may include tertiary amines (e.g., triethylenediamine, dimethylcyclohexylamine, and dimethylethanolamine). Organometallic catalysts may be based on mercury, lead, tin (dibutyltin dilaurate), bismuth (bismuth octanoate), and zinc.

In yet another example, where the polymerizable composition is used to form a thiol-ene polymer, suitable compositions will typically include a polythiol compound and a polyvinyl ("-ene") compound to so form a curable blend. In addition to thiols and vinyl functional groups, further functional groups may be provided to tailor and/or provide additional desirable properties. Therefore, suitable thiol compounds include aliphatic (poly)thiols, aromatic (poly)thiols, and polymeric (poly)thiols.

For example, suitable examples of aliphatic and cycloaliphatic dithiols include 1,2-ethanedithiol, butanedithiol, 1,3-propanedithiol, 1,5-pentanedithiol, 2,3-dimercapto-1-propanol, dithioerythritol, 3,6-dioxa-1,8-octanedithiol, 1,8-octanedithiol hexanedithiol, dithiodiglycol, pentanedithiol, decanedithiol, 2-methyl 1,4 butanedithiol, bis-mercaptoethylphenyl methane, 1,9-nonanedithiol(1,9-dimercaptononane), glycol dimercaptoacetate, 3-mercapto-β,4-dimethyl-cyclohexaneethanethiol, cyclohexane dimethane dithiol, and 3,7-dithia-1,9-nonanedithiol.

Suitable examples of aromatic dithiols include 1,2-benzenedithiol, 1,3-benzenedithiol, 1,4-benzenedithiol, 2,4,6-trimethyl-1,3-benzenedimethanethiol, durene-α1,α2-dithiol, 3,4-dimercaptotoluene, 4-methyl-1,2-benzenedithiol, 2,5-dimercapto-1,3,4-thiadiazole, 4,4'-thiobisbezenedithiol, bis(4-mercaptophenyl)-2,2'-propane (bisphenol dithiol) (made according to the method of Meng Y. Z., Hay. A. S., J. of App. Polym. Sci., V74, 3069-307, 1999), [1,1'-biphenyl]-4,4'-dithiol, and p-xylene-α,α-dithiol, while suitable examples of oligomeric dithiols include difunctional mercapto functional urethane oligomers derived from end capping moieties of hydroxyethyl mercaptan, hydroxypropyl mercaptan, dimercaptopropane, and dimercaptoethane.

Examples of suitable trithiol functional compounds include, trimethylolethane tris-mercaptopropionate, trimethylolpropane tris-mercaptopropionate, trimethylolethane tris-mercaptoacetate, and trimethylolpropane tris-mercaptoacetate glycerol tri(11-mercaptoundecate), trimethylol propane tri(11-mercaptoundecate). A preferred trithiol is tri-methylolpropane tris(2-mercaptopropionate), and examples of suitable tetrafunctional thiols include pentaerythritol tetramercapto propionate, pentaerythritol tetramercapto acetate, and pentathritoltetra(11-mercaptoundecate).

Multi functional thiols can be obtained by reacting thioalkyl carboxylic acids (e.g., thioglycolic acid, mercapto propionic acid, etc.) with high functional alcohols, amines and thiols. Furthermore, multifunctional thiols can be obtained by reacting mercapto alkyl trialkoxy silanes with silanols that may be polymeric or silica based silanols. Still further contemplated multifunctional thiols can be obtained using thiol carboxylic acids in which the carboxylic acid groups are reacted with reactive enes, alcohols, thiols or amines that are multifunctional. Contemplated examples of multifunctional thiols are described in WO 88/02902. Therefore, and among other suitable choices, examples of polythiols include ethylene glycol bis(thioglycolate), ethylene glycol bis(β-mercaptopropionate), trimethylolpropane tris(thioglycolate), trimethylolpropane tris(β-mercaptopropionate), pentaerythritol tetrakis(β-mercaptopropionate), all of which are commercially available. Further contemplated polythiols include polypropylene ether glycol bis(β-mercaptopropionate) which is prepared from polypropylene-ether glycol and β-mercaptopropionic acid by esterification.

With respect to suitable polyvinyl or vinyl compounds, it should be appreciated that all compounds having one or more vinyl functional groups are suitable in conjunction with the teachings presented herein. However, it is generally preferred that the polyvinyl or vinyl compound has at least two, and more preferably at least three, vinyl groups. The vinyl groups may be provided by allyls, allyl ethers, vinyl ethers, acrylates, or other monomers containing vinyl groups. Examples of suitable compounds include trimethylolpropane trivinyl ether, pentaerythritoltriallyl ether, and 1,3,5-triallyl-1,3,5-triazine-2,4,6-trione, as well as cycloalkenyls with a single cyclic, multi cyclic, or fused multicyclic structure (optionally comprising one or more heteroatoms). Examples of multicyclic -enes are described in WO 88/02902.

Regardless of the type of polymer formed in the curing reaction, it should be appreciated that additional reactive groups for crosslinking and/or imparting desired functionalities may be included and especially contemplated reactive groups include acidic groups (and most preferably mono- and dicarboxylic groups), basic groups (e.g., quaternary ammonia groups, ammonium groups, etc.), conjugated diene groups, aromatic vinyl groups, and so forth. It should furthermore be appreciated that such additional groups can be coupled to the terminus of a polymer and/or as pendant groups. Furthermore, it is contemplated that the polymerizable compositions may also include various materials and/or reagents to achieve a desired bio-reactive purpose. For example, the polymerizable compositions presented herein may include EDTA, heparin, citrate, dextrose, solid phases, optionally coated with lectins or antibodies, etc.

Still further, it is generally preferred that contemplated compositions will optionally include one or more thixotropic agents to impart flowability to the composition while the composition is subjected to centrifugation, and all known thixotropic additives are deemed suitable for use herein. However, especially preferred thixotropic additives include fumed silica, micronized calcium silicate hydrate crystals and related compounds as described in U.S. Pat. No. 5,120,775, compositions prepared from dimethyl polysiloxane and a precipitated methylated silica as described in U.S. Pat. No. 4,190,535, and gels formed from a silicone oil, a butadiene resin, a polyester resin, or a butylene resin as described in U.S. Pat. No. 4,957,638. Where desirable, the surface properties can be adjusted to accommodate to specific needs of the polymerizable composition. For example, the hydrophobicity of the additive may be increased or decreased using one or more agents (e.g., using lipophilic or hydrophilic organosilanes or organosiloxanes) and/or one or more types of reactive groups may be introduced to allow covalent binding of the additive polymer components. It should further be noted that contemplated thixotropic additives will advantageously allow the polymerizable composition to remain in a gelled state prior to combination and/or centrifugation with the fluid sample (typically blood). Thus, contemplated polymerizable compositions can remain at the bottom of a collection tube and will not flow out of the tube or to a position near the top of the tube, even if the tube is in an inverted or tiled position. Upon centrifugation the polymerizable composition can then flow to the proper position.

Consequently, and depending on the particular polymerizable composition, it should be recognized that the mechanism of polymerization to the final separator polymer may vary considerably. Therefore, all known mechanisms of polymerization are deemed suitable for use herein. For example, contemplated polymerization mechanisms include radical and cationic polymerization (e.g., using photolabile compounds, radical starters, etc.), condensation polymerization, esterification, amide formation, etc.

With respect to suitable energy sources it is generally preferred that the energy source provides non-particulate energy, more preferably, electromagnetic radiation, and most preferably UV irradiation (e.g., in the range 250 nm to 400 nm). However, it is noted that other irradiation is also deemed suitable, including microwave irradiation, irradiation with visible light, infrared irradiation, radiofrequency irradiation, and ionizing (e.g., beta- or gamma-ray) irradiation. Irradiation is typically delivered through the wall of the tube, but direct fiberoptic delivery to the polymerizable composition is also suitable. For example, collection tubes may be irradiated in the rotor or after centrifugation in a dedicated rack.

Depending on the type of polymerizable composition and reaction, it is noted that all known photoinitiators are deemed suitable. However, particularly preferred photoinitiators include those that may be classified as organic onium salts, and especially as aromatic sulfonium salts (e.g., phenacylsulfonium salts, hydroxyphenylsulfonium salts, sulfoxonium salts, and/or those that are activated by a sensitizer). Still further preferred photoinitiators include organic silicon-containing compounds that produce a silanol upon UV irradiation in the presence of organic aluminum-containing compounds. Additionally contemplated photoinitiators include (a) phosphine oxide photoinitiators (e.g., 2,4,6-trimethylbenzyl-diphenyl-phosphine oxide, bis(2,4,6-trimethylbenzoyl) phenylphosphine oxide, bis(2,6-dimethoxybenzoyl)-2,4,4-trimethyl pentyl phosphine oxide), (b) ketone-based photoinitiators (e.g., hydroxy- and alkoxyalkyl phenyl ketones, 2-benzyl-2-(dimethylamino)-4'-morpholinobutyrophenone, 1-phenyl-2-hydroxy-2-methyl propanone, 2-hydroxy-2-methylpropiophenone, benzophenone, trimethylbenzophenone, methylbenzophenone, 1-hydroxycyclohexylphenyl ketone, isopropyl thioxanthone, 2,2-dimethyl-2-hydroxy-acetophenone, 2,2-dimethoxy-2-phenylacetophenone, 2-methyl-1-[4-(methylthio)phenyl]-2-morpholino-propan-1-one, and thioalkylphenyl morpholinoalkyl ketones), and benzoin ether photoinitiators (e.g., benzoin isopropyl ether, etc.).

With respect to curing time, it should be appreciated that the curing time will depend on the particular composition of the polymerizable composition, reaction conditions, and quantity of photoinitiators and/or photoinhibitors. However, it is generally preferred that the curing time will be adjusted to be less than 10 minutes, more preferably less than 5 minutes, and most preferably less than 1 minute (e.g., less than 30 second, less than 20 seconds, etc.). The term "curing time" as used herein refers to the time needed to achieve at least 85% of the hardness measured 60 minutes after irradiation (or otherwise initiation or acceleration of polymerization). Of course, it should be appreciated that desirable curing times can be adjusted by inclusion of appropriate photoinitiators, irradiation conditions, and optionally photoinhibitors to so obtain a polymer with the desired hardness.

Hardness can be measured using any suitable hardness scale including one of the Shore hardness scales. The Shore 00 hardness scale is used to measure the hardness of soft substances including gels or foams. The Shore A hardness scale is used to measure the hardness of substances having an intermediate hardness including rubbers. The Shore D hardness scale is used to measure the hardness of harder substances including plastics. Although the preceding Shore hardness scales are used for different various substances, the scales all overlap at the low end of their spectrums. Therefore, a value of 10 on the Shore D scale is harder than a value of 10 on the Shore A scale which in turn is harder than a value of 10 on the Shore 00 scale. The separator substance that is formed by polymerization of the polymerizable composition is preferably formulated to harden to at least 1 on the Shore 00 hardness scale, more preferably to at least 10 on the Shore A hardness scale, and most preferably to at least 10 on the Shore D hardness scale. With respect to the hardness of the cured polymer it is generally preferred that the cured polymer has a hardness of at least 10 of a Shore 00, more typically on a Shore A, and most typically Shore D scale.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A blood collection tube for separation of whole blood into a cell-depleted phase and a cell-enriched phase comprising:
    a polymerizable composition having a predetermined density and flowability effective to allow sedimentation of the composition under a centrifugal force to a position between the cell-depleted phase and the cell-enriched phase;
    wherein the polymerizable composition has a composition effective to retain the predetermined flowability during irradiation sterilization, and to allow subsequent UV curing to a hardness of at least 10 on a Shore A hardness scale within ten minutes.

2. The collection tube of claim 1 wherein the density is between 1.02 and 1.06 g/cm$^3$.

3. The collection tube of claim 1 wherein the polymerizable composition is polymerizable by UV curing to a polymer selected from the group consisting of an acrylate polymer, a methacrylate polymer, an epoxy polymer, a polyurethane, and a thiol-ene polymer.

4. The collection tube of claim 3 wherein the polymerizable composition comprises at least one compound selected from the group consisting of a monofunctional acrylate, a bifunctional acrylate, a trifunctional acrylate, a tetrafunctional acrylate, and an acrylate containing oligomer.

5. The collection tube of claim 3 wherein the polymerizable composition comprises at least one compound selected from the group consisting of a monofunctional methacrylate, a bifunctional methacrylate, a trifunctional methacrylate, a tetrafunctional methacrylate, and a methacrylate containing oligomer.

6. The collection tube of claim 3 wherein the polymerizable composition comprises at least one compound selected from the group consisting of a polymer containing a terminal epoxy group, a polymer containing a pendant epoxy group, an epoxy-siloxane resin, an epoxy-polyurethane, an epoxy-polyesters, epichlorohydrin, a polyhydric diol, and a polyhydric polyol.

7. The collection tube of claim 3 wherein the polymerizable composition comprises at least one compound selected from the group consisting of an aromatic isocyanate, an aliphatic isocyanate, a polymer comprising a terminal or pendant isocyanate group, a polymer comprising at least two hydroxyl groups, a polyhydric diol, and a polyhydric polyol.

8. The collection tube of claim 3 wherein the polymerizable composition comprises at least one compound selected from the group consisting of an aliphatic monomeric polythiol, an aliphatic dithiol, a cycloaliphatic dithiol, an aromatic dithiol, a polymeric polythiol, an acrylate, a methacrylate, an alkenyl, and a cycloalkenyl.

9. The collection tube of claim 1 wherein the composition further comprises a photoinitiator and an optional photoinhibitor.

10. The collection tube of claim 9 wherein the photoinitiator is selected from the group consisting of a phosphine oxide photoinitiator, a ketone-based photoinitiator, and a benzoin ether photoinitiator.

11. The collection tube of claim 1 wherein the irradiation sterilization is gamma ray irradiation sterilization.

12. The collection tube of claim 1 wherein the polymerizable composition further comprises silica.

13. The collection tube of claim 1 wherein the polymerizable composition has a composition effective to allow curing without substantial cell entrapment.

14. The collection tube of claim 1 wherein the hardness is achieved upon UV curing over a period of less than five minutes.

15. The collection tube of claim 1 wherein the polymerizable composition has a composition effective to form a fluid-proof barrier between the composition and an inner wall of the collection tube.

16. A method of assisting separation of whole blood in a blood collection tube in a cell-depleted phase and a cell-enriched phase comprising the steps of:

Adding into the collection tube a polymerizable composition having a predetermined density and flowability effective to allow sedimentation of the composition under a centrifugal force to a position between the cell-depleted phase and the cell-enriched phase, wherein the polymerizable composition has a composition effective to retain the predetermined flowability during irradiation sterilization, and to allow subsequent UV curing to a hardness of at least 10 on a Shore A hardness scale within them minutes;

Sterilizing the collection tube and optionally evacuating the collection tube; and Providing instructions to use UV irradiation after centrifugation for a period of less than ten minutes to cure the polymerizable composition to a hardness of at least 10 on a Shore A hardness scale.

17. The method of claim 16 wherein the polymerizable composition is polymerizable by UV curing to a polymer selected from the group consisting of a acrylate polymer, a methacrylate polymer, an epoxy polymer, a polyurethane, and a thiol-ene polymer.

18. The method of claim 16 wherein the composition further comprises a photoinitiator and an optional photoinhibitor.

19. The method of claim 16 wherein UV irradiation is performed in a rotor of a centrifuge.

* * * * *